United States Patent [19]

Innis

[11] Patent Number: 4,975,276
[45] Date of Patent: Dec. 4, 1990

[54] INTERFERON-ALPHA 54

[75] Inventor: Michael A. Innis, Oakland, Calif.

[73] Assignee: Cetus Corporation, Emeryville, Calif.

[21] Appl. No.: 414,051

[22] Filed: Sep. 2, 1982

Related U.S. Application Data

[63] Continuation-in-part of Ser. No. 339,828, Jan. 15, 1982, abandoned.

[51] Int. Cl.$^5$ .................... A61K 37/66; C07K 13/00; C07K 15/26
[52] U.S. Cl. .................................. 424/857; 424/854; 530/351; 435/69.51; 435/811
[58] Field of Search ............... 424/85, 85.7, 85.4; 435/68, 811, 69.51; 260/112 R, 112.5 R; 530/351

[56] References Cited

U.S. PATENT DOCUMENTS

4,289,690  9/1981  Pestka et al. ..................... 424/85
4,801,685  1/1989  Goeddel et al. ................... 424/85.7

FOREIGN PATENT DOCUMENTS

32134   7/1981  European Pat. Off. .
2079291 1/1982  United Kingdom .

OTHER PUBLICATIONS

Pestka, S., Scientific American, Aug. 1983, pp. 37–43.
Lawn, R., et al., Proc. Natl. Acad. Sci., vol. 78, pp. 5435–5439, 1981.
Goeddel, D., et al., Nature, vol. 287, pp. 411–416, 1980.
Nagata, S., et al., Nature, vol. 284, pp. 316–320, 1980.
Streuli, M., et al., Proc. Natl. Acad. Sci., vol. 78, pp. 2848–2852, 1981.
Yelverton, E., et al., Nucleic Acid Research, vol. 9, pp. 731–741, 1981.
Goeddel, D., et al., Nature, vol. 290, pp. 20–26, 1981.
Chemical Abstracts, vol. 94, Abstract No. 63542, 1981.
Colby, C., et al., Annual Review of Microbiology, pp. 333–360, 1971.
Nagata, S., et al., J. Interferon Research, vol. 1, pp. 333–336, 1981.
Pestka, S., Arch. Biochem. Biophy., vol. 221, pp. 1, 18, 23, 32–39, 1983.
Chemical Abstracts, vol. 93, Abstract No. 236612x, 1980.
Chemical Abstracts, vol. 96, Abstract No. 63668b, 1982.
Chemical Abstracts, vol. 96, Abstract 80569r, 1982.

*Primary Examiner*—Margaret Moskowitz
*Assistant Examiner*—D. Bernstein
*Attorney, Agent, or Firm*—Philip L. McGarrigle; Michael A. Innis

[57] ABSTRACT

A new polypeptide, called IFN-α54, produced by *E. coli* transformed with a newly isolated and characterized human IFN-α gene is described. The polypeptide exhibits interferon activities such as antiviral activity, cell growth regulation, and regulation of production of cell-produced substances.

15 Claims, 7 Drawing Sheets

```
         10         20         30         40         50         60
  AGAGCTGAAG GTTCAGAGTC ACCCATCTCA ACAAGTCCAA CAGCATCTGC AACATCTACA
  TCTCGACTTC CAAGTCTCAG TGGGTAGAGT TGTTCAGGTT GTCGTAGACG TTGTAGATGT
         70         80         90        100        110        120
  ATGGCTTTGC CTTTTGCTTT ACTGATGGCC CTGGTGGTGC TCAGCTGCAA GTCAAGCTGC
  TACCGAAACG GAAAACGAAA TGACTACCGG GACCACCACG AGTCGACGTT CAGTTCGACG
        130        140        150        160        170        180
  TCTCTGGACT GTGATCTGCC TCAGACCCAC AGCCTGGGTC ACAGGAGGAC CATGATGCTC
  AGAGACCTGA CACTAGACGG AGTCTGGGTG TCGGACCCAG TGTCCTCCTG GTACTACGAG
        190        200        210        220        230        240
  CTGGCACAAA TGAGGAGAAT CTCTCTTTTC TCCTGTCTGA AGGACAGACA TGACTTCAGA
  GACCGTGTTT ACTCCTCTTA GAGAGAAAAG AGGACAGACT TCCTGTCTGT ACTGAAGTCT
        250        260        270        280        290        300
  TTTCCCCAGG AGGAGTTTGA TGGCAACCAG TTCCAGAAGG CTGAAGCCAT CTCTGTCCTC
  AAAGGGGTCC TCCTCAAACT ACCGTTGGTC AAGGTCTTCC GACTTCGGTA GAGACAGGAG
        310        320        330        340        350        360
  CATGAGGTGA TTCAGCAGAC CTTCAATCTC TTCAGCACAA AGGACTCATC TGTTGCTTGG
  GTACTCCACT AAGTCGTCTG GAAGTTAGAG AAGTCGTGTT TCCTGAGTAG ACAACGAACC
        370        380        390        400        410        420
  GATGAGAGGC TTCTAGACAA ACTCTATACT GAACTTTACC AGCAGCTGAA TGACCTGGAA
  CTACTCTCCG AAGATCTGTT TGAGATATGA CTTGAAATGG TCGTCGACTT ACTGGACCTT
        430        440        450        460        470        480
  GCCTGTGTGA TGCAGGAGGT GTGGGTGGGA GGGACTCCCC TGATGAATGA GGACTCCATC
  CGGACACACT ACGTCCTCCA CACCCACCCT CCCTGAGGGG ACTACTTACT CCTGAGGTAG
        490        500        510        520        530        540
  CTGGCTGTGA GAAAATACTT CCAAAGAATC ACTCTCTACC TGACAGAGAA AAAGTACAGC
  GACCGACACT CTTTTATGAA GGTTTCTTAG TGAGAGATGG ACTGTCTCTT TTTCATGTCG
        550        560        570        580        590        600
  CCTTGTGCCT GGGAGGTTGT CAGAGCAGAA ATCATGAGAT CCTTCTCTTC ATCAAGAAAC
  GGAACACGGA CCCTCCAACA GTCTCGTCTT TAGTACTCTA GGAAGAGAAG TAGTTCTTTG
        610        620        630        640        650        660
  TTGCAAGAAA GGTTAAGGAG GAAGGAATAA GACCTGATCC AACACAGAAA CGACTCCCAT
  AACGTTCTTT CCAATTCCTC CTTCCTTATT CTGGACTAGG TTGTGTCTTT GCTGAGGGTA
        670        680        690        700        710        720
  TGACGACTAC ACCAGCTTGC ACTTTCATGA TCTGCCATTT TAAAGACTCT TGTTTCTGCT
  ACTGCTGATG TGGTCGAACG TGAAAGTACT AGACGGTAAA ATTTCTGAGA ACAAAGACGA
        730        740        750        760        770        780
  ATAACCATAC CATGAGTTGA ATCAAACGCG TCAAGTATTT TCAAGTGTGT TAACGAACAT
  TATTGGTATG GTACTCAACT TAGTTTGCGC AGTTCATAAA AGTTCACACA ATTGCTTGTA
        790        800        810        820        830
  CGTGTTCAGT TGCACAGGAA CTAGTCCTTA CAGATGACTA ACGTGATGGA TCTATTT
  GCACAAGTCA ACGTGTCCTT GATCAGGAAT GTCTACTGAT TGCACTACCT AGATAAA
```

Figure 3

```
1
Met Ala Leu Pro Phe Ala Leu Leu Met Ala Leu Val Val Leu Ser Cys Lys Ser Ser Cys
ATG GCT TTG CCT TTT GCT TTA CTG ATG GCC CTG GTG GTG CTC AGC TGC AAG TCA AGC TGC

21
Ser Leu Asp Cys Asp Leu Pro Gln Thr His Ser Leu Gly His Arg Arg Thr Met Met Leu
TCT CTG GAC TGT GAT CTG CCT CAG ACC CAC AGC CTG GGT CAC AGG AGG ACC ATG ATG CTC

41
Leu Ala Gln Met Arg Arg Ile Ser Leu Phe Ser Cys Leu Lys Asp Arg His Asp Phe Arg
CTG GCA CAA ATG AGG AGA ATC TCT CTT TTC TCC TGT CTG AAG GAC AGA CAT GAC TTC AGA

61
Phe Pro Gln Glu Glu Phe Asp Gly Asn Gln Phe Gln Lys Ala Glu Ala Ile Ser Val Leu
TTT CCC CAG GAG GAG TTT GAT GGC AAC CAG TTC CAG AAG GCT GAA GCC ATC TCT GTC CTC

81
His Glu Val Ile Gln Gln Thr Phe Asn Leu Phe Ser Thr Lys Asp Ser Ser Val Ala Trp
CAT GAG GTG ATT CAG CAG ACC TTC AAT CTC TTC AGC ACA AAG GAC TCA TCT GTT GCT TGG

101
Asp Glu Arg Leu Leu Asp Lys Leu Tyr Thr Glu Leu Tyr Gln Gln Leu Asn Asp Leu Glu
GAT GAG AGG CTT CTA GAC AAA CTC TAT ACT GAA CTT TAC CAG CAG CTG AAT GAC CTG GAA

121
Ala Cys Val Met Gln Glu Val Trp Val Gly Gly Thr Pro Leu Met Asn Glu Asp Ser Ile
GCC TGT GTG ATG CAG GAG GTG TGG GTG GGA GGG ACT CCC CTG ATG AAT GAG GAC TCC ATC

141
Leu Ala Val Arg Lys Tyr Phe Gln Arg Ile Thr Leu Tyr Leu Thr Glu Lys Lys Tyr Ser
CTG GCT GTG AGA AAA TAC TTC CAA AGA ATC ACT CTC TAC CTG ACA GAG AAA AAG TAC AGC

161
Pro Cys Ala Trp Glu Val Val Arg Ala Glu Ile Met Arg Ser Phe Ser Ser Ser Arg Asn
CCT TGT GCC TGG GAG GTT GTC AGA GCA GAA ATC ATG AGA TCC TTC TCT TCA TCA AGA AAC

181
Leu Gln Glu Arg Leu Arg Arg Lys Glu
TTG CAA GAA AGG TTA AGG AGG AAG GAA
```

Figure 5

```
1
GAA TTC CGA CAT CAT AAC GGT TCT GGC AAA TAT TCT GAA ATG AGC TGT TGA CAA TTA ATC
Eco RI

61                                                                          Met Cys
ATC GAA CTA GTT AAC TAG TAC GCA AGT TCA CGT AAA AAG GGT ATC GAT AAG CTT ATG TGT

121
Asp Leu Pro Gln Thr His Ser Leu Gly His Arg Arg Thr Met Met Leu Leu Ala Gln Met
GAT CTG CCT CAG ACC CAC AGC CTG GGT CAC AGG AGG ACC ATG ATG CTC CTG GCA CAA ATG
Sau 3A
181
Arg Arg Ile Ser Leu Phe Ser Cys Leu Lys Asp Arg His Asp Phe Arg Phe Pro Gln Glu
AGG AGA ATC TCT CTT TTC TCC TGT CTG AAG GAC AGA CAT GAC TTC AGA TTT CCC CAG GAG

241
Glu Phe Asp Gly Asn Gln Phe Gln Lys Ala Glu Ala Ile Ser Val Leu His Glu Val Ile
GAG TTT GAT GGC AAC CAG TTC CAG AAG GCT GAA GCC ATC TCT GTC CTC CAT GAG GTG ATT

301
Gln Gln Thr Phe Asn Leu Phe Ser Thr Lys Asp Ser Ser Val Ala Trp Asp Glu Arg Leu
CAG CAG ACC TTC AAT CTC TTC AGC ACA AAG GAC TCA TCT GTT GCT TGG GAT GAG AGG CTT

361
Leu Asp Lys Leu Tyr Thr Glu Leu Tyr Gln Gln Leu Asn Asp Leu Glu Ala Cys Val Met
CTA GAC AAA CTC TAT ACT GAA CTT TAC CAG CAG CTG AAT GAC CTG GAA GCC TGT GTG ATG
Xba I
421
Gln Glu Val Trp Val Gly Gly Thr Pro Leu Met Asn Glu Asp Ser Ile Leu Ala Val Arg
CAG GAG GTG TGG GTG GGA GGG ACT CCC CTG ATG AAT GAG GAC TCC ATC CTG GCT GTG AGA

481
Lys Tyr Phe Gln Arg Ile Thr Leu Tyr Leu Thr Glu Lys Lys Tyr Ser Pro Cys Ala Trp
AAA TAC TTC CAA AGA ATC ACT CTC TAC CTG ACA GAG AAA AAG TAC AGC CCT TGT GCC TGG

541
Glu Val Val Arg Ala Glu Ile Met Arg Ser Phe Ser Ser Ser Arg Asn Leu Gln Glu Arg
GAG GTT GTC AGA GCA GAA ATC ATG AGA TCC TTC TCT TCA TCA AGA AAC TTG CAA GAA AGG

601
Leu Arg Arg Lys Glu ***
TTA AGG AGG AAG GAA TAA GAC CTG ATC CAA CAC AGA AAC GAC TCC CAT TGA CGA CTA CAC

661
CAG CTT GCA CTT TCA TGA TCT GCC ATT TTA AAG ACT CTT GTT TCT GCT ATA ACC ATA CCA
721
TGA GTT GAA TCA AAC GCG TCA AGT ATT TTC AAG TGT GTT
                                                Hinc II
```

Figure 6

IFN-α54 Expression Plasmid

INTERFERON-ALPHA 54

CROSS-REFERENCE TO RELATED APPLICATION

This application is a continuation-in-part of copending U.S. Ser. No 339,828 filed 15 Jan. 1982, now abandoned.

DESCRIPTION

1. Technical Field

The invention is in the field of biotechnology. More particularly it relates to a polypeptide having interferon (IFN) activity, DNA that codes for the polypeptide, a recombinant vector that includes the DNA, a host organism transformed with the recombinant vector that produces the polypeptide, pharmaceutical compositions containing the polypeptide, and therapeutic methods employing the polypeptide.

2. Background Art

IFNs are proteins with antiviral, immunomodulatory, and antiproliferative activities produced by mammalian cells in response to a variety of inducers (see Stewart, W. E., *The Interferon System*, Springer-Verlag, New York, 1979). The activity of IFN is largely species specific (Colby, C., and Morgan, M. J., *Ann. Rev. Microbiol.* 25:333–360 (1971) and thus only human IFN can be used for human clinical studies. Human IFNs are classified into three groups, α, β, and γ, (Nature, 286:110, (1980)). The human IFN-α genes compose a multigene family sharing 85%–95% sequence homology (Goeddel, D. V. et al, Nature 290:20–27 (1981) Nagata, S., et al, *J. Interferon Research* 1:333–336 (1981)). Several of the IFN-α genes have been cloned and expressed in *E. coli* (Nagata, S., et al, Nature 284:316–320 (1980); Goeddel, D. V., et al, Nature 287:411–415 (1980); Yelverton, E., et al, *Nucleic Acids Research,* 9:731–741, (1981); Streuli, M., et al, *Proc Nat Acad Sci (USA),* 78:2848–2852. The resulting polypeptides have been purified and tested for biological activities associated with partially purified native human IFNs and found to possess similar activities. Accordingly such polypeptides are potentially useful as antiviral, immunomodulatory, or antiproliferative agents.

A principal object of the present invention is to provide a polypeptide having interferon activity that is produced by an organism transformed with a newly isolated and newly characterized IFN-α gene. This polypeptide is sometimes referred to herein as IFN-αlb 54. Other objects of the invention are directed to providing the compositions and hosts that are used to produce this polypeptide and to therapeutic compositions and methods that use this polypeptide as an active ingredient.

DISCLOSURE OF THE INVENTION

One aspect of the invention is a polypeptide having interferon activity and comprising the amino acid sequence:

| | |
|---|---|
| CysAspLeuProGln | ThrHisSerLeuGly |
| HisArgArgThrMet | MetLeuLeuAlaGln |
| MetArgArgIleSer | LeuPheSerCysLeu |
| LysAspArgHisAsp | PheArgPheProGln |
| GluGluPheAspGly | AsnGlnPheGlnLys |
| AlaGluAlaIleSer | ValLeuHisGluVal |
| IleGlnGlnThrPhe | AsnLeuPheSerThr |
| LysAspSerSerVal | AlaTrpAspGluArg |
| LeuLeuAspLysLeu | TyrThrGluLeuTyr |
| GlnGlnLeuAsnAsp | LeuGluAlaCysVal |
| MetGlnGluValTrp | ValGlyGlyThrPro |
| LeuMetAsnGluAsp | SerIleLeuAlaVal |
| ArgLysTyrPheGln | ArgIleThrLeuTyr |
| LeuThrGluLysLys | TyrSerProCysAla |
| TrpGluValValArg | AlaGluIleMetArg |
| SerPheSerSerSer | ArgAsnLeuGlnGlu |
| ArgLeuArgArgLys | Glu |

A second aspect of the invention is a DNA unit or fragment comprising a nucleotide sequence that encodes the above described polypeptide.

A third aspect of the invention is a cloning vehicle or vector that includes the above described DNA.

A fourth aspect of the invention is a host that is transformed with the above described cloning vehicle and that produces the above described polypeptide.

A fifth aspect of the invention is a process for producing the above described polypeptide comprising cultivating said transformed host and collecting the polypeptide from the resulting culture.

Another aspect of the invention is a pharmaceutical composition having interferon activity comprising an effective amount of the above described polypeptide admixed with a pharmaceutically acceptable carrier.

Still another aspect of the invention is a method of providing interferon therapy to a human comprising administering a therapeutically effective amount of the above described polypeptide to the human.

BRIEF DESCRIPTION OF THE DRAWINGS

FIG. 3 is the nucleotide sequence of the structural gene coding for IFN-α54 including some of the flanking 5'- and 3'- noncoding regions of the gene. The region coding for preinterferon and the mature polypeptide begins with the ATG codon at position 61 and terminates with the TAA-codon at position 628.

FIG. 5 shows the amino acid sequence of the 23 amino acid signal polypeptide and the 166 amino acid mature IFN-α54 coded for by the gene depicted in FIG. 3. The 189 amino acid sequence is displayed above the corresponding nucleotide sequence. Amino acid 24, cysteine, is the first amino acid of the mature IFN-α54 protein.

FIG. 6 is the DNA sequence of the *E. coli* trp promoter and the gene of FIG. 3 which was inserted between the EcoRI and PvuII sites of the plasmid pBW11. The amino acid sequence of FIG. 5 is written above the corresponding DNA sequence and the location of the restriction sites used in the construction of the expression plasmid are indicated.

MODES FOR CARRYING OUT THE INVENTION

In general terms IFN-α54 was made by identifying and isolating the IFN-α54 gene by screening a library of human genomic DNA with an appropriate IFN-α DNA probe, constructing a vector containing the IFN-α54 gene, transforming microorganisms with the vector, cultivating transformants that express IFN-α54 and collecting IFN-α54 from the culture. A preferred embodiment of this procedure is described below.

DNA PROBE PREPARATION

Total cytoplasmic RNA was extracted from human lymphoblastoid cells, Namalwa, which had been induced for IFN production by pretreatment with 5-bromodeoxyuridine and Newcastle Disease Virus (NDV). The poly(A) (polyadenylic acid)-containing messenger RNA (mRNA) was isolated from total RNA by chromatography on oligo(dT)-cellulose (type 3 from Collaborative Research; Aviv, H., and Leder, P., *Proc Natl Acad Sci (USA)*, 69:1408–1412, (1972)) and enriched for IFN mRNA by density gradient centrifugation on 5%–20% sucrose gradients. Fractions containing IFN mRNA were identified by translating the mRNA by microinjecting aliquots of each fraction into Xenopus oocytes and determining the IFN activity of the products of the translations according to a method described by Colman, A., and Morser, J., *Cell*, 17:517–526 (1979).

The Namalwa cell human IFN enriched mRNA was used to construct complementary DNA (cDNA) clones in *E. coli* by the G/C tailing method using the PstI site of the cloning vector pBR322 (Bolivar, F., et al, *Gene*, 2:95–113 (1977)). A population of transformants containing approximately 50,000 individual cDNA clones was grown in one liter of medium overnight and the total plasmid DNA was isolated therefrom.

Figure 1:
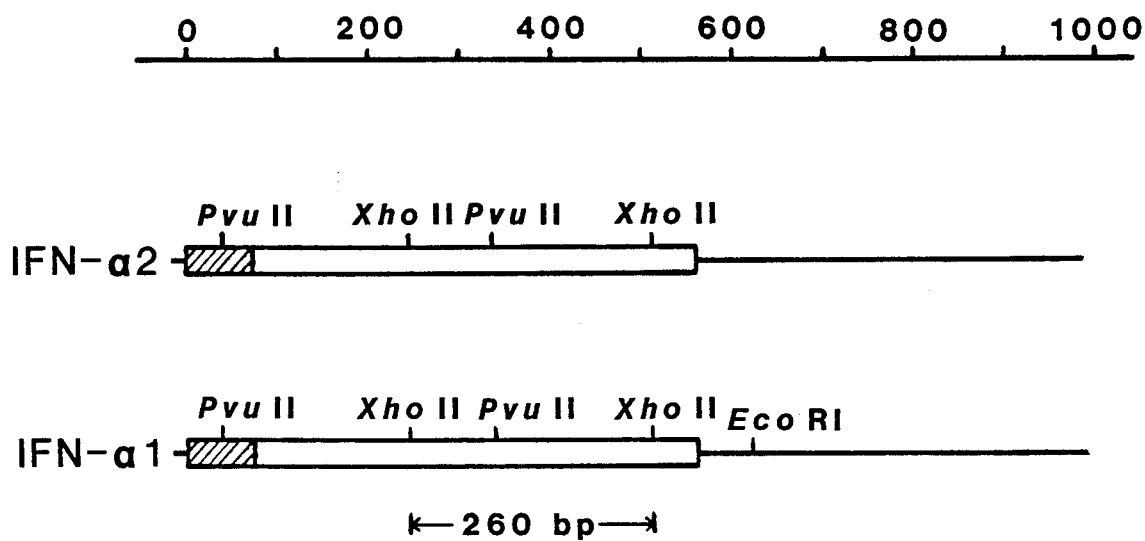
FIG. 1 is a partial restriction map which shows the two XhoII restriction sites that produce a homologous 260 base pair DNA fragment from the IFN-α1 and IFN-α2 structural genes. Data for this map are from Streuli, M., et al *Science,* 209:1343–1347 (1980).

The sequences of two IFN-α clones (IFN-α1 and IFN-α2) have been published (Streuli, M., et al, *Science*, 209:1343–1347 (1980)). Examination of the DNA sequences of these two clones revealed that the restriction enzyme XhoII would excise a 260 bp fragment from either the IFN-α1 or the IFN-α2 gene (see FIG. 1). XhoII was prepared in accordance with the process described by Gingeras, T. R., and Roberts, R. J., *J Mol Biol*, 118:113–122 (1978).

One mg of the purified total plasmid DNA preparation was digested with XhoII and the DNA fragments were separated on a preparative 6% polyacrylamide gel. DNA from the region of the gel corresponding to 260 bp was recovered by electroelution and recloned by ligation into the BamHI site of the single strand bacteriophage m13:mp7. Thirty-six clones were picked at random and the single stranded DNA isolated therefrom and sequenced. The DNA sequences of four of these clones were homologous to known IFN-α DNA sequences. Clone mp7:α-260, with a DNA sequence identical to IFN-α1 DNA (Streuli, M. et al, *Science*, 209:1343–1347 (1980)) was chosen as a highly specific hybridization probe for identifying additional IFN-α DNA sequences. This clone is hereinafter referred to as the "260 probe."

Screening of Genomic DNA Library

In order to isolate other IFN-α gene sequences, a $^{32}$P-labelled 260 probe was used to screen a library of human genomic DNA by in situ hybridization. The human gene bank, prepared by Lawn, R. M., et al, *Cell*, 15:1157–1174 (1978), was generated by partial cleavage of fetal human DNA with HaeIII and AluI and cloned into bacteriophage λ Charon 4A with synthetic EcoRI linkers. Approximately 800,000 clones were screened, of which about 160 hybridized with the 260 probe. Each of the 160 clones was further characterized by restriction enzyme mapping and comparison with the published restriction maps of 10 chromosomal IFN genes (Nagata, S., et al, *J Interferon Research*, 1:333–336 (1981)). One of the clones, hybrid phage λ4A:α54 containing a 16 kb insert, was characterized as follows. A DNA preparation of λ4A:α54 was cleaved with HindIII, BglII, and EcoRI respectively, the fragments separated on an agarose gel, transferred to a nitrocellulose filter (Southern, E. M., *J Mol Biol* 98:503–517 (1977)) and hybridized with $^{32}$P-labelled 260 probe. This procedure localized the IFN-α54 gene to a 3.9 kb EcoRI restriction fragment which was then isolated and recloned, in both orientations, by ligation of the fragment into EcoRI cleaved m13:mp7. The two subclones are designated mp7:α54-1 and mp7:α54-2. The -1 designation indicates that the single-stranded bacteriophage contains insert DNA complementary to the mRNA (the minus strand) and the -2 designation indicates that the insert DNA is the same sequence as the mRNA (the plus strand).

Sequencing of the IFN-α54 Gene

Figure 2:
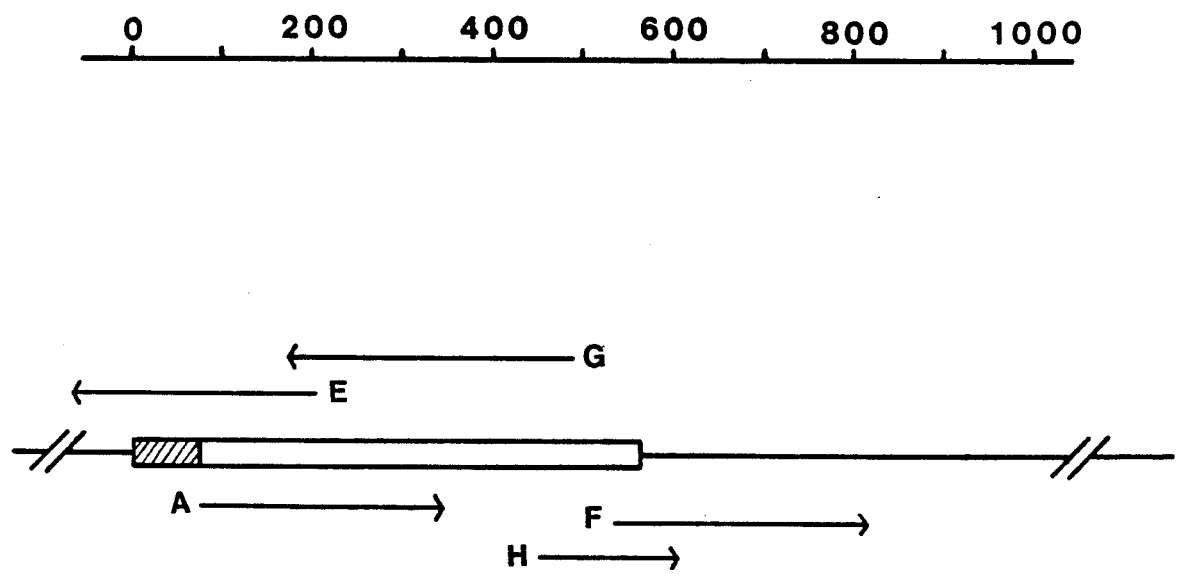
FIG. 2 depicts the sequencing strategy used to obtain the complete DNA sequence of the IFN-α54 gene coding region. Bacteriophage mp7:α54-1 DNA served as the template for sequences obtained with primers A, H and F and bacteriophage mp7:α54-2 DNA was the template for sequences obtained with primers E and G. The crosshatched area of the gene depicts the region that encodes the 23 amino acid signal peptide and the open box depicts the region that encodes the mature polypeptide. The scale, in base pairs, is numbered with 0 representing the ATG start codon of preinterferon. The arrows indicate the direction and extent of sequencing with each primer.
Figure 4:
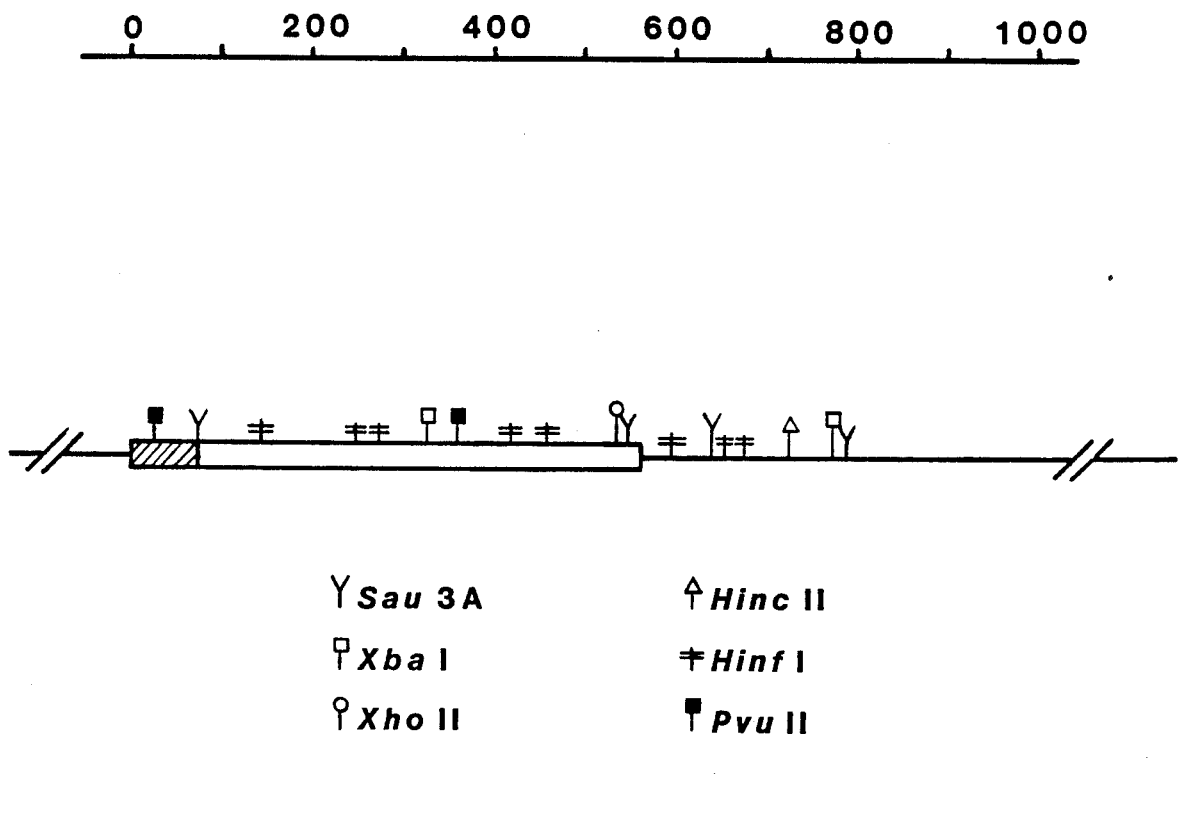
FIG. 4 is a partial restriction map of the coding region of the IFN-α54 gene. The crosshatching represents the region that encodes the 23 amino acid signal peptide and the open box represents the gene coding sequence for the mature polypeptide. The scale, in base pairs, is numbered with 0 representing the ATG start codon of preinterferon.

The Sanger dideoxy-technique was used to determine the DNA sequence of the IFN-α54 gene. The strategy employed is diagrammed in FIG. 2, the DNA sequence thus obtained is given in FIG. 3, and a partial restriction enzyme map of the IFN-α54 gene is illustrated in FIG. 4. Unlike many genes from eukaryotic organisms, but analogous to other IFN chromosomal genes which have been characterised 10 (Nagata, S., et al, *Nature*, 287:401–408 (1980); Lawn, R. M., et al, *Science*, 212:1159–1162 (1981); Lawn, R. M., et al, *Nucleic Acids Res.*, 9:1045–1052 (1981); Nagata, S., et al, *J Interferon Research*, 1:333–336 (1981); Lawn, R. M., et al, *Proc Natl Acad Sci (USA)*, 78:5435–5439 (1981)), the DNA sequence of this gene demonstrates that it lacks introns. Homology to protein sequence information from these published IFN-α genes made it possible to determine the correct translational reading frame and thus allowed the entire 166 amino acid sequence of IFN-α54 to be predicted from the DNA sequence as well as a precursor segment, or signal peptide, of 23 amino acids (FIG. 5). The DNA sequence of the IFN-α54 gene and the amino acid sequence predicted therefrom differ substantially from the other known IFN-α DNA and IFN-α amino acid sequences.

Plasmid Preparation and Host Transformation

Assembly of the plasmid for direct expression of the IFN-α54 gene involved replacing the DNA fragment encoding the 23 amino acid signal polypeptide of preinterferon with a 120 bp EcoRI/Sau3A promoter fragment (E.coli trp promoter, operator, and trp leader ribosome binding site preceding an ATG initiation codon) and using the naturally occurring HincII site, 139 bp 3'-of the TAA translational stop codon, to insert the gene into a cloning vehicle derived from the plasmid pBR322. The complete DNA sequence of the promoter and gene fragments inserted between the EcoRI and PvuII sites of pBR322 is shown in FIG. 6 which also shows the exact location of relevant cloning sites. Details of the construction are described below.

Figure 7:
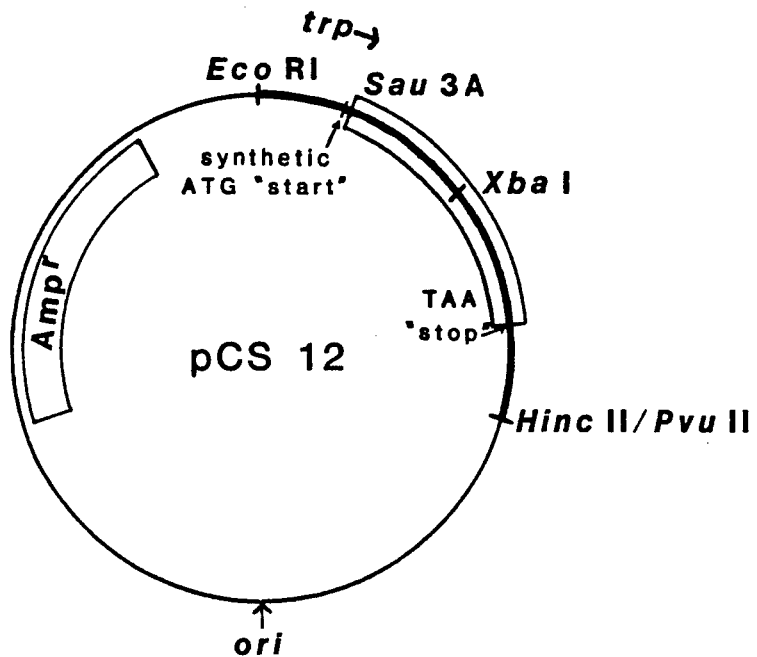
FIG. 7 is a diagram of the expression plasmid, pCS12.

The coding region for mature IFN-α54 encompasses a Sau3A site between codons for amino acids 2 and 3 and an XbaI site between codons for amino acids 81 and 83. The 239 bp Sau3A to XbaI fragment was isolated on a 6% polyacrylamide gel following a Sau3A/XbaI double-digest of the 3.9 kb EcoRI genomic fragment. This fragment was ligated to the 120 bp EcoRI/Sau 3A promoter fragment. The promoter fragment contained a synthetic HindIII restriction site, ATG initiation codon, the initial cysteine codon (TGT) and a Sau 3A "sticky end". The ligation mixture was digested with EcoRI and XbaI to enrich for the desired product and ligated with an EcoRI/XbaI digested vector fragment pBW11 (derived from pBR322 which contained unique EcoRI and XbaI restriction sites). The ligation mixture was used to transform E.coli MM294 (Backman, K., et al, Proc Natl Acad Sci (USA), 73:4174–4178 (1976)). The desired correct transformation product, designated pCS10, was identified by restriction enzyme mapping. DNA from this intermediate plasmid was prepared, digested with XbaI and PvuII, and the large fragment containing the promoter and the 5'-portion of the gene was used as a vector for reconstituting the 3'-end of the gene. Referring to the restriction enzyme sites shown in FIG. 6, the 397 base pair Xba to HincII fragment encompassing the 3'-codon region, the TAA translational stop codon and an additional 139 base pairs of 3'-noncoding sequence was isolated on a 4% polyacrylamide gel following an XbaI/HincII double-digest of the 3.9 kb genomic EcoRI fragment. This XbaI to HincII fragment was ligated to the Xba/PvuII digested pCS10, the ligation mixture was used to transform E.coli MM294, and correct transformants (3 out of 100 screened) were identified by restriction enzyme mapping. FIG. 7 is a diagram of one of the final expression constructs obtained, which is designated pCS12. Other prokaryotic hosts such as bacteria other than E.coli may, of course, be transformed with this or other suitable constructs to replicate the IFN-α54 gene and/or to produce IFN-α54.

Cultivation of Transformants

Bacteria transformed with the IFN-α54 gene may be cultivated in an appropriate growth medium, such as a minimum essential medium, that satisfies the nutritional and other requirements needed to permit the bacteria to grow and produce IFN-α54. If the bacteria are such that the protein is contained in their cytoplasm, the IFN-α54 may be extracted from the cells by lysing the cells such as by sonication and/or treatment with a strong anionic solubilizing agent such as sodium dodecyl sulfate. Further purification of the extract may be achieved by affinity chromatography, electrophoresis, or other protein purification techniques.

IFN-α54 produced in accordance with the invention is believed to be distinct from the corresponding native protein in several respects. Firstly, because the IFN-α54 gene was expressed by bacterial hosts that utilize N-formyl-methionine and/or methionine to initiate translation, some or all of the bacterially produced IFN-α54 molecules are preceded by an N-formyl-methionine or methionine group. Some of the N-formyl-methionine or methionine groups could be removed by natural in vivo bacterial cleavage mechanisms. This would result in a mixture of molecules, some of which would include an initial N-formyl-methionine or methionine and others that would not. All such IFN-α54 molecules, those containing an initial N-formyl-methionine or methionine, those not containing an N-formyl-methionine or methionine and any mixture thereof, are encompassed by the present invention. Secondly, the amino acid residues of the bacterially produced polypeptide are unsubstituted whereas the residues of the native protein may be substituted with sugar groups, ACTH or other moieties. Also, native IFN-α extracts consist of mixtures of various IFN molecules whereas the bacterially produced IFN-α54 is homogeneous; that is, bacterially produced IFN-α54 does not contain functionally related polypeptides. Accordingly, the invention contemplates producing IFN-α54-containing compositions having biological activity that is attributable solely to IFN-α54 and/or said terminal N-formyl-methionine or methionine derivatives thereof.

Biological Testing of IFN-α54

IFN-α54-containing cell sonicates were tested in vitro and found to have the following activities: (1) inhibition of viral replication of vesicular stomatitis virus (VSV) and herpes simplex virus-1 (HSV-1); (2) inhibition of tumor cell growth; (3) inhibition of colony formation by tumor cells in soft agar; (4) activation of natural killer (NK) cells; (5) enhancement of the level of 2',5'-oligoadenylate synthetase (2',5'-A); and (6) enhancement of the double-stranded RNA-dependent protein kinase. The sonicates were active in inhibiting viral infection in both human and other mammalian cells such as hamster, monkey, mouse, and rabbit cells.

The tests show that IFN-α54 exhibits antiviral activity against DNA and RNA viruses, cell growth regulating activity, and an ability to regulate the production of intracellular enzymes and other cell-produced substances. Accordingly, it is expected IFN-α54 may be used to treat viral infections with a potential for interferon therapy such as chronic hepatitis B infection, ocular, local, or systemic herpes virus infections, influenza and other respiratory tract virus infections, rabies and other viral zoonoses, arbovirus infections, and slow virus diseases such as Kuru and sclerosing panencephalitis. It may also be useful for treating viral infections in immunocompromised patients such as herpes zoster and varicella, cytomegalovirus, Epstein-Barr virus infection, herpes simplex infections, rubella, and progressive multifocal leukoencephalopathy. Its cell growth regulating activity makes it potentially useful for treating tumors and cancers such as osteogenic sarcoma, multiple myeloma, Hodgkin's disease, nodular, poorly differentiated lymphoma, acute lymphocytic leukemia, breast carcinoma, melanoma, and nasopharyngeal carcinoma. The fact that IFN-α54 increases protein kinase and 2',5'-oligoadenylate synthetase indicates it may also increase synthesis of other enzymes or cell-produced substances commonly affected by IFNs such as histamine, hyaluronic acid, prostaglandin E, tRNA methylase, and aryl hydrocarbon hydrolase. Similarly, it may be useful to inhibit enzymes commonly inhibited by IFNs such as tyrosine amino transferase, glycerol-3-phosphate dehydrogenase glutamine synthetase, ornithine decarboxylase, S-adenosyl-1-methionine decarboxylase, and UDP-N-acetylglucosamine-dolichol monophosphate transferase. The ability of the IFN-α54 to stimulate NK cell activity is indicative that it may also possess other activities such as the abilities to induce macrophage activity and antibody production and to effect cell surface alterations such as changes in plasma membrane density or cell surface charge, altered capacity to bind substances such as cholera toxin, concanavalin A and thyroid-stimulating hormone, and change in the exposure of surface gangliosides.

Pharmaceutical compositions that contain IFN-α54 as an active ingredient will normally be formulated with an appropriate solid or liquid carrier depending upon the particular mode of administration being used. For instance, parenteral formulations are usually injectable fluids that use pharmaceutically and physiologically acceptable fluids such as physiological saline, balanced salt solutions, or the like as a vehicle. Oral formulations, on the other hand, may be solid, e.g. tablet or capsule, or liquid solutions or suspensions. IFN-α54 will usually be formulated as a unit dosage form that contains in the range of $10^4$ to $10^7$ international units, more usually $10^6$ to $10^7$ international units, per dose.

IFN-α54 may be administered to humans in various manners such as orally, intravenously, intramuscularly, intraperitoneally, intranasally, intradermally, and subcutaneously. The particular mode of administration and dosage regimen will be selected by the attending physician taking into account the particulars of the patient, the disease and the disease state involved. For instance, viral infections are usually treated by daily or twice daily doses over a few days to a few weeks; whereas tumor or cancer treatment involves daily or multidaily doses over months or years. IFN-α54 therapy may be combined with other treatments and may be combined with or used in association with other chemotherapeutic or chemopreventive agents for providing therapy against viral infections, neoplasms, or other conditions against which it is effective. For instance, in the case of herpes virus keratitis treatment, therapy with IFN has been supplemented by thermocautery, debridement and trifluorothymidine therapy.

Modifications of the above described modes for carrying out the invention, such as, without limitation, use of alternative vectors, alternative expression control systems in the vector, and alternative host microorganisms and other therapeutic or related uses of IFN-α54, that are obvious to those of ordinary skill in the biotechnology, pharmaceutical, medical and/or related fields are intended to be within the scope of the following claims.

I claim:

1. A recombinantly produced polypeptide having interferon activity and comprising the amino acid sequence of IFN-α54, :

| | |
|---|---|
| CysAspLeuProGln | ThrHisSerLeuGly |
| HisArgArgThrMet | MetLeuLeuAlaGln |
| MetArgArgIleSer | LeuPheSerCysLeu |

-continued

| | |
|---|---|
| LysAspArgHisAsp | PheArgPheProGln |
| GluGluPheAspGly | AsnGlnPheGlnLys |
| AlaGluAlaIleSer | ValLeuHisGluVal |
| IleGlnGlnThrPhe | AsnLeuPheSerThr |
| LysAspSerSerVal | AlaTrpAspGluArg |
| LeuLeuAspLysLeu | TyrThrGluLeuTyr |
| GlnGlnLeuAsnAsp | LeuGluAlaCysVal |
| MetGlnGluValTrp | ValGlyGlyThrPro |
| LeuMetAsnGluAsp | SerIleLeuAlaVal |
| ArgLysTyrPheGln | ArgIleThrLeuTyr |
| LeuThrGluLysLys | TyrSerProCysAla |
| TrpGluValValArg | AlaGluIleMetArg |
| SerPheSerSerSer | ArgAsnLeuGlnGlu |
| ArgLeuArgArgLys | Glu. |

2. The polypeptide of claim 1 wherein the polypeptide consists essentially of said amino acid sequence.

3. The polypeptide of claim 1 or 2 wherein the initial cysteine residue of the amino acid sequence is preceded by an N-formyl-methionine group.

4. The polypeptide of claim 1 or 2 wherein the amino acid residues of said sequence are unsubstituted.

5. Recombinantly produced IFN-α54.

6. A composition having interferon activity and comprising a mixture of:

(a) a precombinantly produced polypeptide having the amino acid sequence

| | |
|---|---|
| CysAspLeuProGln | ThrHisSerLeuGly |
| HisArgArgThrMet | MetLeuLeuAlaGln |
| MetArgArgIleSer | LeuPheSerCysLeu |
| LysAspArgHisAsp | PheArgPheProGln |
| GluGluPheAspGly | AsnGlnPheGlnLys |
| AlaGluAlaIleSer | ValLeuHisGluVal |
| IleGlnGlnThrPhe | AsnLeuPheSerThr |
| LysAspSerSerVal | AlaTrpAspGluArg |
| LeuLeuAspLysLeu | TyrThrGluLeuTyr |
| GlnGlnLeuAsnAsp | LeuGluAlaCysVal |
| MetGlnGluValTrp | ValGlyGlyThrPro |
| LeuMetAsnGluAsp | SerIleLeuAlaVal |
| ArgLysTyrPheGln | ArgIleThrLeuTyr |
| LeuThrGluLysLys | TyrSerProCysAla |
| TrpGluValValArg | AlaGluIleMetArg |
| SerPheSerSerSer | ArgAsnLeuGlnGlu |
| ArgLeuArgArgLys | Glu | and;

(b) a polypeptide having said amino acid sequence wherein the initial cysteine residue of the sequence is preceded by an N-formyl-methionine or methionine group.

7. The composition of claim 6 wherein the amino acid residues of said sequence are unsubstituted.

8. A composition having interferon activity comprising a polypeptide having the amino acid sequence

| | |
|---|---|
| CysAspLeuProGln | ThrHisSerLeuGly |
| HisArgArgThrMet | MetLeuLeuAlaGln |
| MetArgArgIleSer | LeuPheSerCysLeu |
| LysAspArgHisAsp | PheArgPheProGln |
| GluGluPheAspGly | AsnGlnPheGlnLys |
| AlaGluAlaIleSer | ValLeuHisGluVal |
| IleGlnGlnThrPhe | AsnLeuPheSerThr |
| LysAspSerSerVal | AlaTrpAspGluArg |
| LeuLeuAspLysLeu | TyrThrGluLeuTyr |
| GlnGlnLeuAsnAsp | LeuGluAlaCysVal |
| MetGlnGluValTrp | ValGlyGlyThrPro |
| LeuMetAsnGluAsp | SerIleLeuAlaVal |
| ArgLysTyrPheGln | ArgIleThrLeuTyr |
| LeuThrGluLysLys | TyrSerProCysAla |
| TrpGluValValArg | AlaGluIleMetArg |
| SerPheSerSerSer | ArgAsnLeuGlnGlu |

| -continued | |
|---|---|
| ArgLeuArgArgLys | Glu | or a mixture of said polypeptide and a polypeptide having said sequence wherein the initial cysteine residue is preceded by an N-formyl-methionine or methionine group wherein the interferon activity of the composition is attributable to said polypeptide or to said mixture.

9. A pharmaceutical composition for providing interferon therapy to a mammal comprising an effective amount of the polypeptide of claim 1, 2, or 5 admixed with a pharmaceutically acceptable vehicle or carrier.

10. A pharmaceutical composition for providing interferon therapy to a mammal comprising an effective amount of the composition of claims 6 or 8 admixed with a pharmaceutically acceptable vehicle or carrier.

11. A method of providing interferon therapy to a human comprising administering a therapeutically effective amount of the polypeptide of claim 1, 2 or 5 to said human.

12. A method of providing interferon therapy to a human comprising administering a therapeutically effective amount of the composition of claim 6 or 8 to said human.

13. The method of claim 12 wherein the therapy is for treating a viral infection, providing cell growth regulation, or regulating the production of a cell-produced substance.

14. The method of claim 13 wherein the therapy is for treating a viral infection, providing cell growth regulation, or regulating the production of a cell-produced substance.

15. A method of providing antiviral therapy to a mammal comprising administering a viral infection inhibiting amount of the polypeptide of claim 1, 2 or 5 to the mammal.

* * * * *